United States Patent [19]

Elbe et al.

[11] Patent Number: 4,562,198

[45] Date of Patent: * Dec. 31, 1985

[54] COMBATING FUNGI WITH SUBSTITUTED AZOLYL-TETRAHYDRO-FURAN-2-YLI-DENE-METHANE DERIVATIVES

[75] Inventors: Hans-Ludwig Elbe, Wuppertal; Manfred Jautelat; Karl H. Büchel, both of Burscheid; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[*] Notice: The portion of the term of this patent subsequent to Dec. 11, 2001 has been disclaimed.

[21] Appl. No.: 658,344

[22] Filed: Oct. 5, 1984

[30] Foreign Application Priority Data

Oct. 11, 1983 [DE] Fed. Rep. of Germany ....... 3336859

[51] Int. Cl.$^4$ ................... A01N 43/50; A01N 43/653; C07D 233/60; C07D 249/08
[52] U.S. Cl. .................... 514/383; 514/397; 548/262; 548/336
[58] Field of Search ............... 548/262, 336; 424/269, 424/273 R; 514/383, 397

[56] References Cited

U.S. PATENT DOCUMENTS 4,228,177 10/1980 Hoehn ................................ 548/336
4,465,680  8/1984 Kraatz et al. ....................... 548/336
4,487,776 12/1984 Elbe et al. ......................... 424/273 R

FOREIGN PATENT DOCUMENTS 44276  1/1982 European Pat. Off. ............ 548/336

OTHER PUBLICATIONS

*Remington's Pharmaceutical Sciences*, Oslo et al., Edits., 14th Ed., 1970, pp. 528-529.

Primary Examiner—Richard A. Schwartz
Assistant Examiner—Kurt G. Briscoe
Attorney, Agent, or Firm—Sprung Horn Kramer & Woods

[57] ABSTRACT

Azolyl-tetrahydrofuran-2-ylidene-methanes of the formula

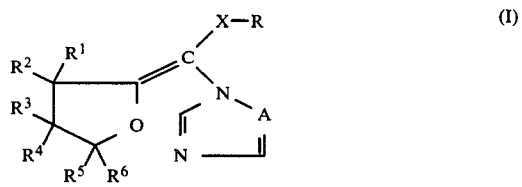

in which
A represents a nitrogen atom or the CH group;
X represents oxygen, sulphur or the SO or SO$_2$ group;
R represents optionally substituted aryl;
R$^1$ and R$^6$ are identical or different and represent hydrogen, alkyl, halogenoalkyl or halogen, a maximum of up to 3 substituents representing halogen or halogenoalkyl, with the proviso that R$^1$ and R$^2$ are not at the same time methyl if X represents oxygen;
R$^1$ and R$^2$, together with the carbon atom to which they are bonded, represent optionally substituted cycloalkyl or
R$^2$ and R$^3$, together with the carbon atoms to which they are bonded, represent optionally substituted cycloalkyl, or addition products thereof with acids or metal salts. Some new intermediates are also shown. The end products are fungicides.

10 Claims, No Drawings

COMBATING FUNGI WITH SUBSTITUTED AZOLYL-TETRAHYDRO-FURAN-2-YLIDENE-METHANE DERIVATIVES

The present invention relates to new substituted azolyl-tetrahydrofuran-2-ylidene-methane derivatives, a process for their preparation and their use as fungicides.

It has already been disclosed that certain azolylalkenols, such as, for example, 1-(imidazol-1-yl)- or 1-(1,2,4-triazol-1-yl)-2-phenoxy-4,4-dimethyl-1-penten-3-ols which are substituted in the phenoxy part, have good fungicidal properties (U.S. Pat. No. 4,360,528). It is also already known that disulphides, such as, for example, zinc ethylene-1,2-bisdithiocarbamidate, are good agents for combating fungal plant diseases (compare R. Wegler, "Chemie der Pflanzenschutz- und Schadlingsbekampfungsmittel" ("Chemistry of the Plant Protection Agents and Agents for Combating Pests"), Volume 2, page 59 et seq., Springer-Verlag 1970).

However, the action of these compounds is not always completely satisfactory in certain fields of indication, especially when low amounts and concentrations are applied.

New substituted azolyl-tetrahydrofuran-2-ylidenemethane derivatives of the general formula (I)

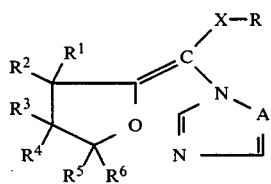

in which
A represents a nitrogen atom or the CH group;
X represents oxygen, sulphur or the SO or $SO_2$ group;
R represents optionally substituted aryl;
$R^1$ to $R^6$ are identical or different and represent hydrogen, alkyl, halogenoalkyl or halogen, a maximum of up to 3 substituents representing halogen or halogenoalkyl, with the proviso that $R^1$ and $R^2$ are not at the same time methyl if X represents oxygen;
$R^1$ and $R^2$, together with the carbon atom to which they are bonded, represent optionally substituted cycloalkyl or
$R^2$ and $R^3$, together with the carbon atoms to which they are bonded, represent optionally substituted cycloalkyl, and acid addition salts and metal salt complexes thereof have been found.

The compounds of the formula (I) can exist in two geometric isomer forms, depending on the arrangement of the groups bonded to the double bond; they are preferentially obtained in a varying isomer ratio. The present invention relates both to the individual isomers and to the isomer mixtures.

It has furthermore been found that the substituted azolyl-tetrahydrofuran-2-ylidene-methane derivatives of the formula (I) are obtained by a process in which halogeno-(thio)ether-ketones of the formula (II)

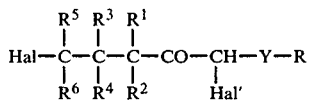

in which
R and $R^1$ to $R^6$ have the abovementioned meaning,
Y represents oxygen or sulphur and
Hal and Hal' represent halogen, preferably chlorine or bromine, are reacted with imidazole or 1,2,4-triazole in the presence of a diluent and in the presence of an acid-binding agent, and, if appropriate, the substituted azolyl-tetrahydrofuran-2-ylidene-methane derivatives thus obtained, of the formula (Ia)

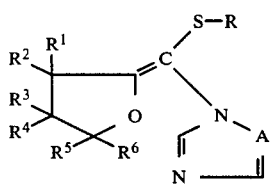

in which
A, R and $R^1$ to $R^6$ have the abovementioned meaning,
are oxidized by known methods in the customary manner.

If appropriate, an acid or a metal salt can then be added onto the compounds of the formula (I) thus obtained.

It has also been found that the new substituted azolyl-tetrahydrofuran-2-ylidene-methane derivatives of the formula (I) have powerful fungicidal properties.

Surprisingly, the compounds of the formula (I) according to the invention exhibit better fungicidal actions than the 1-(imidazol-1-yl)- or 1-(1,2,4-triazol-1-yl)-2-phenoxy-4,4-dimethyl-1-penten-3-ols which are substituted in the phenoxy part and are known from the prior art, and than zinc ethylene 1,2-bisdithiocarbamidate, which is likewise known. The active compounds according to the invention thus represent an enrichment of the art.

Formula (I) provides a general definition of the substituted azolyl-tetrahydrofuran-2-ylidene-methane derivatives according to the invention. Preferably, in this formula,
A represents a nitrogen atom or the CH group;
X represents oxygen, sulphur or the SO or $SO_2$ group;
R represents phenyl which is optionally mono-, di- or tri-substituted by identical or different substituents, substituents which may be mentioned being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as fluorine and chlorine atoms, alkoxycarbonyl with 1 to 4 carbon atoms in the alkyl part, alkoximinoalkyl with 1 to 4 carbon atoms in the alkoxy part and 1 or 2 carbon atoms in the alkyl part, nitro, cyano and phenyl and phenoxy which are optionally substituted by halogen and/or alkyl with 1 or 2 carbon atoms;

$R^1$ to $R^6$, which can be identical or different, represent hydrogen, straight-chain or branched alkyl with 1 to 4 carbon atoms or halogenoalkyl with 1 or 2 carbon atoms and 1 to 5 identical or different halogen atoms, such as fluorine and chlorine atoms, up to a maximum of 3 substituents representing halogenoalkyl, with the proviso that $R^1$ and $R^2$ do not at the same time represent methyl if X represents oxygen; or $R^3$ to $R^6$, which can be identical or different, also represent halogen, up to a maximum of 3 substituents having this meaning; or $R^1$ and $R^2$, together with the carbon atom to which they are bonded, represent cycloalkyl which has 4 to 7 carbon atoms and is optionally substituted by alkyl with 1 or 2 carbon atoms; or $R^2$ and $R^3$, together with the carbon atom to which they are bonded, represent cycloalkyl which has 4 to 7 carbon atoms and is optionally substituted by alkyl with 1 or 2 carbon atoms. Particularly preferred compounds of the formula (I) are those in which A represents a nitrogen atom or the CH group;

X represents oxygen, sulpur or the SO or $SO_2$ group;

R represents phenyl which is optionally mono-, di- or tri-substituted by identical or different substituents, substituents which may be mentioned being: fluorine, chlorine, bromine, methyl, ethyl, tert.-butyl, methoxy, methylthio, trifluoromethyl, trifluoromethoxy, trifluoromethylthio, methoxycarbonyl, ethoxycarbonyl, methoximinomethyl, 1-methoximinoethyl, nitro, cyano and phenyl and phenoxy which are optionally substituted by chlorine and/or methyl;

$R^1$ to $R^6$ which can be identical or different, represent hydrogen, methyl, ethyl or halogenomethyl with 1 to 3 identical or different halogen atoms, such as fluorine and chlorine atoms, a maximum of three substituents representing halogenomethyl, with the proviso that $R^1$ and $R^2$ do not at the same time represent methyl if X represents oxygen; or $R^3$ to $R^6$, which can be identical or different, also represent fluorine, chlorine or bromine, up to a maximum of three substituents having this meaning; or $R^1$ and $R^2$, together with the carbon atom to which they are bonded, represent cyclopentyl or cyclohexyl; or $R^2$ and $R^3$, together with the carbon atom to which they are bonded, represent cyclopentyl or cyclohexyl.

The following compounds of the general formula (I) may be mentioned specifically, in addition to the preparation examples:

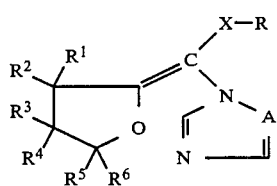

(I)

(wherein A represents either a nitrogen atom or the CH group).

| $R^1$ | $R^2$ | $R^3$ | $R^4$ | $R^5$ | $R^6$ | X | R |
|---|---|---|---|---|---|---|---|
| $C_2H_5$ | $CH_3$ | H | H | H | H | O | phenyl |
| $C_2H_5$ | $CH_3$ | H | H | H | H | S | phenyl |
| $(CH_2)_5$ | | H | H | H | H | O | 4-Cl-phenyl |
| $C_2H_5$ | $CH_3$ | H | H | H | H | O | 3-CH₃-4-Cl-phenyl |
| $C_2H_5$ | $CH_3$ | H | H | H | H | O | 3-CH₃-4-Cl-phenyl |
| $C_2H_5$ | $CH_3$ | H | H | H | H | O | 3-CH₃-4-F-phenyl |
| $C_2H_5$ | $CH_3$ | H | H | H | H | O | 3-CH₃-4-F-phenyl |
| $C_2H_5$ | $CH_3$ | H | H | H | H | O | 3-Cl-4-CH₃-phenyl |
| $C_2H_5$ | $CH_3$ | H | H | H | H | O | 3-Cl-4-CH₃-phenyl |
| $C_2H_5$ | $CH_3$ | H | H | H | H | O | 3-F-4-CH₃-phenyl |
| $C_2H_5$ | $CH_3$ | H | H | H | H | O | 3-F-4-CH₃-phenyl |
| $C_2H_5$ | $CH_3$ | H | H | H | H | O | 3-Cl-4-F-phenyl |
| $C_2H_5$ | $CH_3$ | H | H | H | H | O | 3-F-4-Cl-phenyl |
| $C_2H_5$ | $CH_3$ | H | H | H | H | O | 3,4-di-Cl-phenyl |

-continued

| R¹ | R² | R³ | R⁴ | R⁵ | R⁶ | X | R |
|---|---|---|---|---|---|---|---|
| C₂H₅ | CH₃ | H | H | H | H | O | 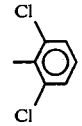 2,3-dichlorophenyl |
| C₂H₅ | CH₃ | H | H | H | H | O | 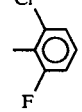 2-Cl, 3-F phenyl |
| C₂H₅ | CH₃ | H | H | H | H | O |  4-Br phenyl |
| C₂H₅ | CH₃ | H | H | H | H | O | 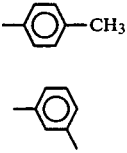 4-CH₃ phenyl |
| C₂H₅ | CH₃ | H | H | H | H | O | 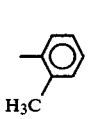 3-CH₃ phenyl |
| C₂H₅ | CH₃ | H | H | H | H | O | 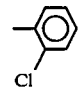 2-CH₃ phenyl |
| C₂H₅ | CH₃ | H | H | H | H | O | 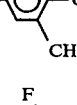 2-Cl phenyl |
| C₂H₅ | CH₃ | H | H | H | H | O | 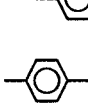 2,4-diCH₃ phenyl |
| C₂H₅ | CH₃ | H | H | H | H | O |  2-F phenyl |
| C₂H₅ | CH₃ | H | H | H | H | O | 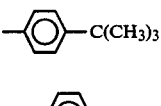 biphenyl |
| C₂H₅ | CH₃ | H | H | H | H | O | 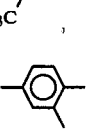 4-Cl biphenyl |
| C₂H₅ | CH₃ | H | H | H | H | O | 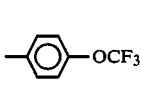 4-(4-Cl phenoxy)phenyl |
| C₂H₅ | CH₃ | H | H | H | H | O |  4-t-Bu phenyl |
| C₂H₅ | CH₃ | H | H | H | H | O | 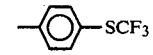 2,4-diCH₃ phenyl |
| C₂H₅ | CH₃ | H | H | H | H | O | 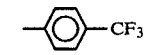 3-Br, 4-F phenyl |
| C₂H₅ | CH₃ | H | H | H | H | O |  4-OCF₃ phenyl |
| C₂H₅ | CH₃ | H | H | H | H | O |  4-SCF₃ phenyl |
| C₂H₅ | CH₃ | H | H | H | H | O |  4-CF₃ phenyl |
| C₂H₅ | CH₃ | H | H | H | H | O | 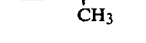 2,4-diCl phenyl |
| C₂H₅ | CH₃ | H | H | H | H | O |  4-CH=NOCH₃ phenyl |
| C₂H₅ | CH₃ | H | H | H | H | O |  4-C(CH₃)=NOCH₃ phenyl |
| C₂H₅ | CH₃ | H | H | H | H | S |  3-Cl, 4-F phenyl |
| C₂H₅ | CH₃ | H | H | H | H | S | 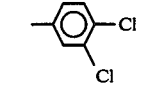 4-Cl, 3-F phenyl |
| C₂H₅ | CH₃ | H | H | H | H | S | 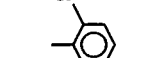 3,4-diCl phenyl |
| C₂H₅ | CH₃ | H | H | H | H | S | 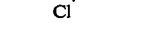 2,3-diCl phenyl |
| C₂H₅ | CH₃ | H | H | H | H | S | 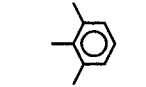 2-Cl, 3-F phenyl |
| C₂H₅ | CH₃ | H | H | H | H | S |  4-Br phenyl |
| C₂H₅ | CH₃ | H | H | H | H | S |  4-CH₃ phenyl |
| C₂H₅ | CH₃ | H | H | H | H | S |  3-CH₃ phenyl |
| C₂H₅ | CH₃ | H | H | H | H | S |  2-CH₃ phenyl |
| C₂H₅ | CH₃ | H | H | H | H | S | 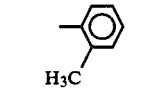 2-Cl phenyl |

| R¹ | R² | R³ | R⁴ | R⁵ | R⁶ | X | R |
|---|---|---|---|---|---|---|---|
| C₂H₅ | CH₃ | H | H | H | H | S | 2,3-dimethylphenyl |
| C₂H₅ | CH₃ | H | H | H | H | S | 2-fluorophenyl |
| C₂H₅ | CH₃ | H | H | H | H | S | 4-biphenyl |
| C₂H₅ | CH₃ | H | H | H | H | S | 4'-chloro-4-biphenyl |
| C₂H₅ | CH₃ | H | H | H | H | S | 4-(4-chlorophenoxy)phenyl |
| C₂H₅ | CH₃ | H | H | H | H | S | 4-tert-butylphenyl |
| C₂H₅ | CH₃ | H | H | H | H | S | 2,4-dimethylphenyl |
| C₂H₅ | CH₃ | H | H | H | H | S | 3-bromo-4-fluorophenyl |
| C₂H₅ | CH₃ | H | H | H | H | S | 4-trifluoromethoxyphenyl |
| C₂H₅ | CH₃ | H | H | H | H | S | 4-trifluoromethylthiophenyl |
| C₂H₅ | CH₃ | H | H | H | H | S | 4-trifluoromethylphenyl |
| C₂H₅ | CH₃ | H | H | H | H | S | 3-chloro-4-fluorophenyl |
| C₂H₅ | CH₃ | H | H | H | H | S | 4-(methoxyiminomethyl)phenyl |
| C₂H₅ | CH₃ | H | H | H | H | S | 4-(1-methoxyiminoethyl)phenyl |
| C₂H₅ | CH₃ | H | H | H | H | S | 3-chloro-4-fluorophenyl |
| C₂H₅ | CH₃ | H | H | H | H | S | 3,4-dichlorophenyl |
| C₂H₅ | C₂H₅ | H | H | H | H | O | 4-chlorophenyl |
| C₂H₅ | C₂H₅ | H | H | H | H | O | 2,4-dichlorophenyl |
| C₂H₅ | C₂H₅ | H | H | H | H | O | 3-chloro-4-fluorophenyl |
| C₂H₅ | C₂H₅ | H | H | H | H | O | 4-fluorophenyl |
| C₂H₅ | C₂H₅ | H | H | H | H | S | 4-chlorophenyl |
| C₂H₅ | C₂H₅ | H | H | H | H | S | 2,4-dichlorophenyl |
| C₂H₅ | C₂H₅ | H | H | H | H | S | 3-chloro-4-fluorophenyl |
| C₂H₅ | C₂H₅ | H | H | H | H | S | 4-fluorophenyl |
| C₂H₅ | CH₃ | H | H | H | H | S | 3-methyl-4-chlorophenyl |
| C₂H₅ | CH₃ | H | H | H | H | S | 2-chloro-4-methylphenyl |
| C₂H₅ | CH₃ | H | H | H | H | S | 3-methyl-4-fluorophenyl |
| C₂H₅ | CH₃ | H | H | H | H | S | 2-methyl-4-fluorophenyl |
| C₂H₅ | CH₃ | H | H | H | H | S | 3-chloro-4-methylphenyl |
| C₂H₅ | CH₃ | H | H | H | H | S | 3-chloro-4-methylphenyl |
| C₂H₅ | CH₃ | H | H | H | H | S | 2-fluoro-4-methylphenyl |

| R¹ | R² | R³ | R⁴ | R⁵ | R⁶ | X | R |
|---|---|---|---|---|---|---|---|
| C₂H₅ | CH₃ | H | H | H | H | S | 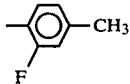 |

Addition products of acids and those substituted azolyltetrahydrofuran-2-ylidene-methane derivatives of the formula (I) in which the substituents A, X, R and R¹ to R⁶ have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids, and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II to IV and of sub-groups I and II and IV to VIII and those substituted azolyl-tetrahydrofuran-2-ylidene-methane derivatives of the formula (I) in which the substituents A, X, R and R¹ to R⁶ have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid.

If, for example, 1-bromo-1-(4-chlorophenylthio)-5-chloro-3,3-dimethyl-2-pentanone and imidazole are used as starting substances, the course of the reaction can be represented by the following equation:

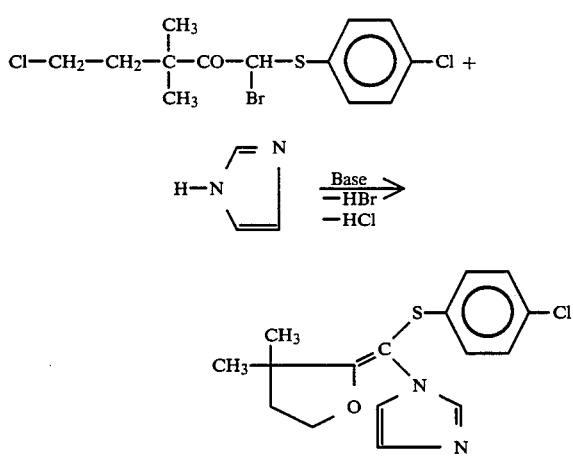

If, for example, 4-chlorophenylthio-(imidazol-1-yl)-3,3-dimethyltetrahydrofuran-2-ylidene-methane and hydrogen peroxide in glacial acetic acid are used as starting substances, the course of the reaction in the oxidation according to the invention can be represented by the following equation:

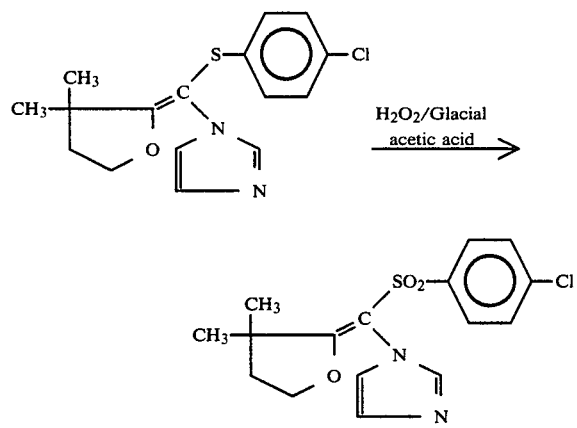

Formula (II) provides a general definition of the halogeno-(thio)ether-ketones to be used as starting substances in carrying out the process according to the invention. In this formula, R and R¹ to R⁶ preferably represent the radicals which have already been mentioned as preferred for these substituents in connection with the description of the substances of the formula (I) according to the invention.

The halogeno-(thio)ether-ketones of the formula (II) are not yet known; however, they can be prepared by known processes, by reacting halogenoketones of the formula (III)

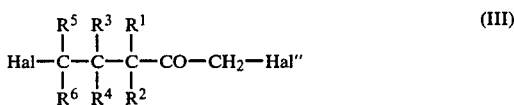

in which
R¹ to R⁶ and Hal have the abovementioned meaning and
Hal" represents halogen, preferably chlorine or bromine,
with known (thio)phenols of the formula (IV)

in which
R and Y have the abovementioned meaning,
in the customary manner and replacing the remaining active hydrogen atom in the (thio)ether-ketones formed, of the formula (V)

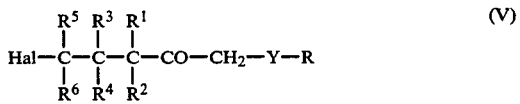

in which
Hal, R, R¹ to R⁶ and Y have the abovementioned meaning,
by halogen in the customary manner (compare also the preparation examples). If appropriate, the halogeno-(thio)ether-ketones of the formula (II) can be further reacted directly, without being isolated.

Halogenoketones of the formula (III) are known (U.S. Ser. No. 460,687, filed Jan. 24, 1983, now pending, corresponding to German Published Specification 3,204,788), and they can be obtained by the processes mentioned therein, by reacting 2-chloromethylene-tetra-hydrofurans of the formula (VI)

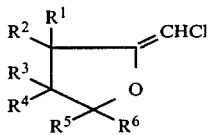

in which
R$^1$ to R$^6$ have the abovementioned meaning,
with acid compounds of the formula (VII)

in which
Hal has the abovementioned meaning,
if appropriate in the presence of an inert organic solvent, such as, for example, toluene or methylene chloride, at temperatures between 20° and 150° C.

The 2-chloromethylene-tetrahydrofurans of the formula (VI) are likewise not yet known; however, they can be obtained in a known manner (compare DE-OS (German Published Specification) 3,204,692), for example by reacting 1,1,5-trichloro-pentene derivatives of the formula (VIII)

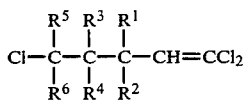

in which
R$^1$ to R$^6$ have the abovementioned meaning,
or 1,1,1,5-tetrachloro-pentane derivatives of the formula (IX)

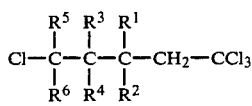

in which
R$^1$ to R$^6$ have the abovementioned meaning,
with carboxylates, such as, for example, anhydrous sodium acetate, and with bases, such as, for example, sodium methylate, in the presence of an inert organic solvent, such as, for example, dimethylformamide, at the reflux temperature.

Certain halogenoketones of the formula (III) can also be obtained by reacting corresponding (unsaturated) ketones with halogenating agents, such as, for example, bromine, hydrogen bromide or sulphuryl chloride, in the customary manner (in this context, compare also the preparation examples).

Possible diluents for the reaction according to the invention are inert organic solvents. These include, preferably, ketones, such as diethyl ketone and, in particular, acetone and methyl ethyl ketone; nitriles, such as propionitrile, in particular acetonitrile; alcohols, such as ethanol or isopropanol; ethers, such as tetrahydrofuran or dioxane; aromatic hydrocarbons, such as toluene, benzene or chlorobenzene; formamides, such as, in particular, dimethylformamide; and halogenated hydrocarbons.

The reaction according to the invention is carried out in the presence of an acid-binding agent. All the inorganic or organic acid-binding agents which can customarily be used may be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and furthermore pyridine and diazabicyclooctane. An appropriate excess of azole is preferably used.

The reaction temperatures can be varied within a substantial range in the process according to the invention. In general, the reaction is carried out between about 20° and about 150° C., preferably at 60° to 120° C.

In carrying out the reaction according to the invention, 1 to 4 moles of azole and 1 to 4 moles of acid-binding agent are preferably employed per mole of the compound of the formula (II). To isolate the compounds of the formula (I), the solvent is distilled off and the residue is worked up in the customary manner.

The reaction temperatures can be varied within a substantial range in carrying out the oxidation according to the invention. In general, the oxidation is carried out between about −50° and 100° C., preferably between −30° and 80° C.

In carrying out the oxidation according to the invention, about 1 to 5 moles of oxidizing agent are employed per mole of the compounds of the formula (Ia) according to the invention. If 1 mole of oxidizing agent is used, such as m-chloroperbenzoic acid in methylene chloride or hydrogen peroxide in acetic acid or acetic anhydride, at temperatures between −30° C. and +30° C., the compounds of the formula (I) according to the invention containing the —SO— grouping are preferentially formed. If an excess of oxidizing agent is used at higher temperatures (10° to 80° C.), the compounds of the formula (I) according to the invention with the —SO$_2$— grouping are preferentially formed. The oxidation products are isolated in the customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The metal salt complexes of the compounds of the formula (I) can be obtained in a simple manner by customary processes, thus, for example, by dissolving the metal salt in alcohol, for example ethanol, and adding the solution to the compounds of the formula (I). The metal salt complexes can be isolated in a known manner, for example by filtration, and if appropriate purified by recrystallization.

The compounds of the formula (I) according to the invention for X=O or S can also be obtained by a process in which
(a) halogenoketones of the formula (III) are reacted with imidazole or 1,2,4-triazole under the conditions of the process according to the invention and the azolyl-tetrahydrofuran-2-ylidene-methanes thus obtained, of the formula (X)

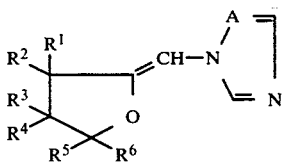

in which

A and $R^1$ to $R^6$ have the abovementioned meaning,
are reacted first with halogen, in particular with bromine, and then with (thio)phenols of the formula (IV), in each case in the customary manner; or (b) 2-chloromethylene-tetrahydrofurans of the formula (VI) are reacted with (thio)phenols of the formula (IV) in the customary manner and the (thio)phenoxytetrahydrofuran-2-ylidene-methanes thus obtained, of the formula (XI)

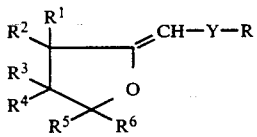

in which

R, $R^1$ to $R^6$ and Y have the abovementioned meaning,
are then reacted first with halogen, in particular with bromine, in the customary manner and then with imidazole or 1,2,4-triazole, under the conditions of the process according to the invention.

The azolyl-tetrahydrofuran-2-ylidene-methanes of the formula (X) and the (thio)phenoxytetrahydrofuran-2-ylidene-methanes of the formula (XI) are new; they are generally interesting intermediates.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as against the powdery mildew of cucumber causative organism (*Spaerotheca fuliginea*); Botrytis species, such as against the grey mould causative organism (*Botrytis cinerea*); cereal diseases, such as *Erysiphe graminis*, rusts, *Cochliobolus sativus* or *Pyrenophora teres*; and rice diseases, such as *Pyricularia oryzae* and *Pellicularia sasakii.* The substances according to the invention also exhibit a broad and good in vitro fungicidal action spectrum.

It should be emphazised that the substances according to the invention not only have a protective action but in some cases are also systemic. Thus, it is possible to protect plants from fungal attack if the active compounds are fed to the above-ground parts of the plant via the soil and the root or via the seed.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

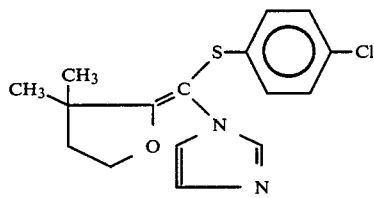
(I-1)

64.9 g (0.94 mole) of imidazole and 129.7 g (0.94 mole) of potassium carbonate are dissolved in 1,300 ml of toluene. 173.9 g (0.47 mole) of 1-bromo-1-(4-chlorophenylthio)-5-chloro-3,3-dimethyl-2-pentanone in 360 ml of toluene are added dropwise to this mixture at 80° C. The reaction mixture is subsequently stirred at 90° C. for 15 hours and is cooled, and the inorganic residue is filtered off with suction. The filtrate is washed with water, dried over sodium sulphate and concentrated. The residue is recrystallized from diethyl ether. 61.4 g (40.8% of theory) of 4-chlorophenylthio-(imidazol-1-yl)-(3,3-dimethyltetrahydrofuran-2-ylidene)-methane of melting point 134° C. are obtained.

Preparation of the starting substance

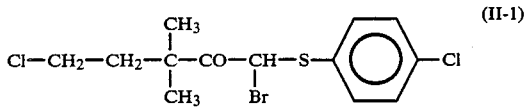
(II-1)

137 g (0.47 mole) of 1-(4-chlorophenylthio)-5-chloro-3,3-dimethyl-2-pentanone are dissolved in 1,000 ml of chloroform. 75.3 g (0.47 mole) of bromine are added dropwise at room temperature such that the solution is always decolorized. The reaction mixture is then subsequently stirred at room temperature for 1 hour and is concentrated by distilling off the solvent. 172.7 g (99.3% of theory) of 1-bromo-1-(4-chlorophenylthio)-5-chloro-3,3-dimethyl-2-pentanone of refractive index $n_D^{20}$ 1.5796 are obtained.

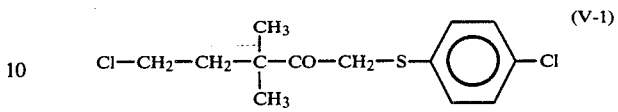
(V-1)

86.7 g (0.6 mole) of 4-chlorothiophenol and 82.8 g (0.6 mole) of potassium carbonate in 500 ml of toluene are heated under reflux for 2 hours, using a water separator. 91.5 g (0.5 mole) of 1,5-dichloro-3,3-dimethyl-2-pentanone in 200 ml of toluene are then added at 100° C. The reaction mixture is stirred at 100° C. for 5 hours and is then allowed to cool, and is stirred with 500 ml of water. The organic phase is separated off, washed with dilute sodium hydroxide solution and with water, dried over sodium sulphate and concentrated. 137.4 g (94.4% of theory) of 1-(4-chlorophenylthio)-5-chloro-3,3-dimethyl-2-pentanone of refractive index $n_D^{20}$ 1.5628 are obtained.

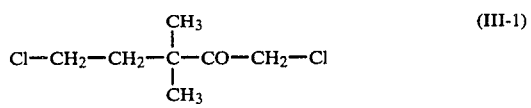
(III-1)

A powerful stream of hydrogen chloride from a cylinder is passed into 476 g (3.25 moles) of 2-chloromethylene-3,3-dimethyltetrahydrofuran, while cooling with ice. The gas is absorbed completely and the internal temperature rises up to 30° C. When the reaction mixture is completely saturated with hydrogen chloride, it is subsequently stirred at room temperature for 2 hours. Excess hydrogen chloride is first stripped off under a waterpump, and the mixture is then distilled under a good vacuum. 531 g (90% of theory) of 1,5-dichloro-3,3-dimethyl-2-pentanone of boiling point 85°-90° C./0.3 mbar are obtained.

(VI-1)

806 g (4 moles) of 1,1,5-trichloro-3,3-dimethyl-1-pentene are heated under reflux with 360 g (4.4 moles) of anhydrous sodium acetate in 1 liter of dimethylformamide for 6 hours. After cooling to about 100° C., 1.6 liter (8 moles) of 30% strength sodium methylate solution in methanol are added dropwise and the mixture is heated under reflux for a further 4 hours. The cold solution is poured into water and extracted several times with methylene chloride.

After the solution has been dried and the solvent has been distilled off, 654 g of product remain, which are fractionated over a column. 522 g (89% of theory) of 2-chloromethylene-3,3-dimethyltetrahydrofuran of boiling point 84°-87° C./20 mbar are obtained.

Example 2

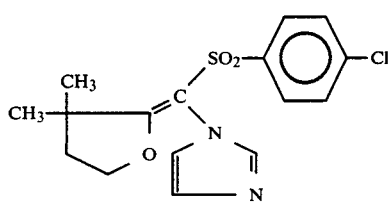
(I-2)

20 g (0.062 mole) of (4-chlorophenylthio)-(imidazol-1-yl)-(3,3-dimethyl-tetrahydrofuran-2-ylidene)-methane (Example I-1) and 28 g (0.25 mole) of 30% strength hydrogen peroxide in 200 ml of glacial acetic acid are stirred at 50° C. for 20 hours. The reaction mixture is then poured into 1.5 liter of water and extracted with methylene chloride. The organic phase is dried over sodium sulphate and concentrated. 10.7 g (49% of theory) of (4-chlorophenylsulphonyl)-(imidazol-1-yl)-(3,3-dimethyltetrahydrofuran-2-ylidene)-methane of melting point 192°–194° C. are obtained.

Example 3

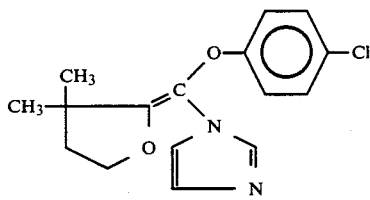
(I-3)

69.9 g (0.19 mole) of 1-bromo-1-(4-chlorophenoxy)-5-chloro-3-ethyl-3-methyl-2-pentanone, 26.2 g (0.38 mole) of imidazole and 52.4 g (0.38 mole) of potassium carbonate in 500 ml of toluene are heated at 90° C. for 10 hours. The reaction mixture is then allowed to cool and is poured onto 500 ml of water. The organic phase is separated off, washed with water, dried over sodium sulphate and concentrated. The residue is purified by column chromatography (ethyl acetate/cyclohexane=3:1). 8.5 g (14% of theory) of (4-chlorophenoxy)-(imidazol-1-yl)-(3-ethyl-3-methyltetrahydrofuran-2-ylidene)-methane of refractive index $n_D^{20}$ 1.5552 are obtained.

Preparation of the starting substance

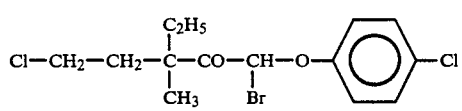
(II-2)

110 g (0.38 mole) of 1-(4-chlorophenoxy)-5-chloro-3-ethyl-3-methyl-2-pentanone are dissolved in 400 ml of chloroform. 60.8 g (0.38 mole) of bromine are added dropwise at room temperature such that the solution is always decolorized. The reaction mixture is then subsequently stirred at room temperature for 30 minutes and concentrated by distilling off the solvent. 138.5 g (99% of theory) of 1-bromo-1-(4-chlorophenoxy)-5-chloro-3-ethyl-3-methyl-2-pentanone of refractive index $n_D^{20}$ 1.5250 are obtained.

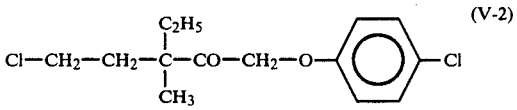
(V-2)

79.7 g (0.62 mole) of 4-chlorophenol and 85.6 g (0.62 mole) of potassium carbonate in 600 ml of toluene are heated under reflux for 2 hours, using a water separator. 104 g (0.53 mole) of 1,5-dichloro-3-ethyl-3-methyl-2-pentanone in 100 ml of toluene are then added at 70° C. The reaction mixture is stirred at 100° C. for 5 hours and is then allowed to cool and is stirred with 500 ml of water. The organic phase is separated off, washed with dilute sodium hydroxide solution and with water, dried over sodium sulphate and concentrated. 110 g (71.8% of theory) of 1-(4-chlorophenoxy)-5-chloro-3-ethyl-3-methyl-2-pentanone of refractive index $n_D^{20}$ 1.5092 are obtained.

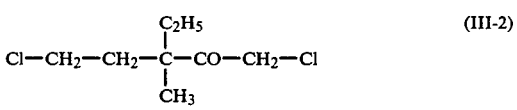
(III-2)

64 g (0.4 mole) of 2-chloromethylene-3-ethyl-3-methyl-tetrahydrofuran are saturated with hydrogen chloride gas at 10° to 20° C., while cooling with ice. After the mixture has been left to stand at room temperature for 2 hours, excess hydrogen chloride is stripped off and the residue is distilled. 60 g (81% of theory) of 1,5-dichloro-3-ethyl-3-methyl-2-pentanone of boiling point 92°–101° C./0.05 mbar are obtained.

(VI-2)

1,260 g (5 moles) of 3-ethyl-3-methyl-1,1,1,5-tetrachloropentane and 902 g (11 moles) of anhydrous sodium acetate are heated under reflux in 4 liter of dimethylformamide for 10 hours. 2.2-liters (11 moles) of 30% strength sodium methylate solution are then added dropwise and the mixture is heated under reflux for 4 hours. The reaction solution is diluted with water and extracted by shaking with methylene chloride. The organic phase is dried over sodium sulphate and concentrated. The residue is distilled. 640 g (80% of theory) of 2-chloromethylene-3-ethyl-3-methyl-tetrahydrofuran of boiling point 100° C. 16 mbar are obtained.

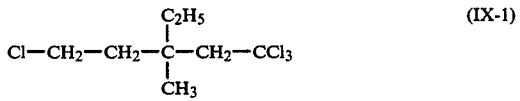
(IX-1)

2,180 g (22.5 moles) of 1,1-dichloroethane are initially introduced into the reaction vessel at −70° C., 75 g of powdered aluminum chloride are added and 1,160 g (7.5 moles) of 1,3-dichloro-3-methylpentane are then added dropwise. The reaction mixture is stirred at −70° C. for 4 hours and is then poured onto ice and dilute hydrochloric acid. It is extracted with methylene chloride and the organic phase is dried over sodium sulphate and concentrated. The residue is distilled. 1,572 g (83% of theory) of 3-ethyl-3-methyl-1,1,1,5-tetrachloropentane of boiling point 85° C./0.1 mbar are obtained.

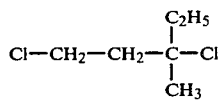

245 g (24.26 moles) of 3-methyl-1-penten-3-ol are added to 4 liters of concentrated hydrochloric acid, with vigorous stirring. Hydrogen chloride gas is then passed in at 20° C. until the mixture is saturated. The organic phase is separated off, dried over sodium sulphate and fractionated. 2,323 g (62% of theory) of 1,3-dichloro-3-methylpentane of boiling point 58°-64° C./16 mbar are obtained.

Example 4

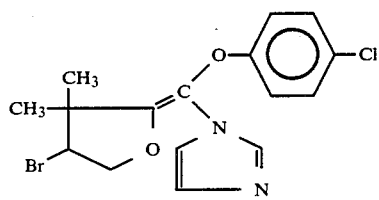

35 g (0.5 mole) of imidazole and 103.5 g (0.75 mole) of potassium carbonate are dissolved in 700 ml of toluene at 60° C. 132 g (0.269 mole) of 1-(4-chlorophenoxy)-3,3-dimethyl-1,4,5-tribromo-2-pentanone in 100 ml of toluene are added dropwise to this solution in the course of 20 minutes. The reaction mixture is subsequently stirred at 90° C. for 10 hours and cooled and water is added. The organic phase is separated off, washed with water dried over sodium sulphate and concentrated. The residue is purified by column chromatography (silica gel; ethyl acetate/cyclohexane=3:1). 10.6 g (10% of theory) of (4-chlorophenoxy)-(imidazol-1-yl)-(4-bromo-3,3-dimethyltetrahydrofuran-2-ylidene)-methane of refractive index $n_D^{20}$ 1.5837 are obtained.

Preparation of the starting substance

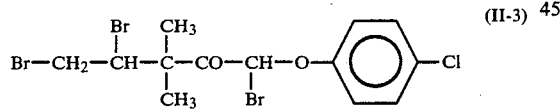

107 g (0.269 mole) of 1-(4-chlorophenoxy)-4,5-dibromo-3,3-dimethyl-2-pentanone are dissolved in 400 ml of chloroform. 43 g (0.269 mole) of bromine are added dropwise at room temperature such that the solution is always decolorized. The mixture is then subsequently stirred at room temperature for 30 minutes, washed with water, dried over sodium sulphate and concentrated. 128 g (99% of theory) of 1-(4-chlorophenoxy)-3,3-dimethyl-1,4,5-tribromo-2-pentanone of refractive index $n_D^{20}$ 1.5472 are obtained.

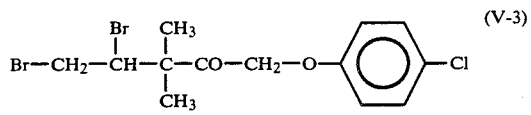

70.7 g (0.55 mole) of 4-chlorophenol and 75.9 g (0.55 mole) of potassium carbonate are heated under reflux in 500 ml of toluene for 2 hours, using a water separator. 133 g (0.433 mole) of 1-chloro-4,5-dibromo-3,3-dimethyl-2-pentanone in 100 ml of toluene are then added at 70° C. The reaction mixture is stirred at 100° C. for 5 hours and is then allowed to cool, and is washed with water and dilute sodium hydroxide solution, dried over sodium sulphate and concentrated. 109.2 g (63.3% of theory) of 1-(4-chlorophenoxy)-4,5-dibromo-3,3-dimethyl-2-pentanone of refractive index $n_D^{20}$ 1.5363 are obtained.

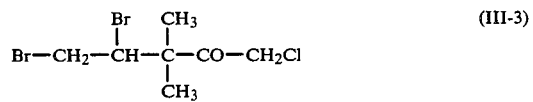

59 g (0.4 mole) of 1-chloro-3,3-dimethyl-4-penten-2-one are initially introduced into 200 ml of methylene chloride. A solution of 320 g (0.4 mole) of bromine in 200 ml of methylene chloride is added dropwise at −70° C. The mixture is subsequently stirred at room temperature for 15 minutes and is concentrated by distilling off the solvent in vacuo. 121 g (98.7% of theory) of crude 1-chloro-4,5-dibromo-3,3-dimethyl-2-pentanone are obtained and are further reacted directly.

The following compounds of the general formula (I)

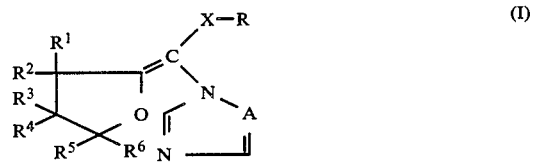

can be obtained in a corresponding manner according to the process conditions described:

| Example No. | $R^1$ | $R^2$ | $R^3$ | $R^4$ | $R^5$ | $R^6$ | X | R | A | Melting point (°C.) or $n_D^{20}$ |
|---|---|---|---|---|---|---|---|---|---|---|
| 5 | $C_2H_5$ | $CH_3$ | H | H | H | H | O | ⟨Cl-phenyl⟩ | CH | 1.5524 |
| 6 | $C_2H_5$ | $CH_3$ | H | H | H | H | O | ⟨F-phenyl⟩ | CH | 1.5393 |

-continued

| Example No. | $R^1$ | $R^2$ | $R^3$ | $R^4$ | $R^5$ | $R^6$ | X | R | A | Melting point (°C.) or $n_D^{20}$ |
|---|---|---|---|---|---|---|---|---|---|---|
| 7 | $C_2H_5$ | $CH_3$ | H | H | H | H | O | 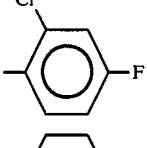 | CH | 78 |
| 8 | $CH_3$ | $CH_3$ | H | H | H | H | S | 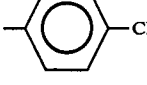 | N | 104 (Form A) |
| 9 | $CH_3$ | $CH_3$ | H | H | H | H | S | 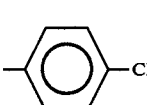 | N | 176 (Form B) |
| 10 | $CH_3$ | $CH_3$ | H | H | H | H | $SO_2$ | 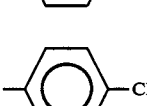 | N | 134 |
| 11 | $C_2H_5$ | $CH_3$ | H | H | H | H | S | 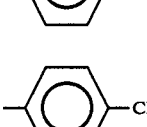 | CH | 200 ($\times$ HCl) |
| 12 | $C_2H_5$ | $CH_3$ | H | H | H | H | O | 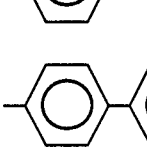 | CH | 1.5906 |

Form A and B: The two possible geometric isomers.

Use Examples

The compounds shown below are used as comparison substances in the examples which follow:

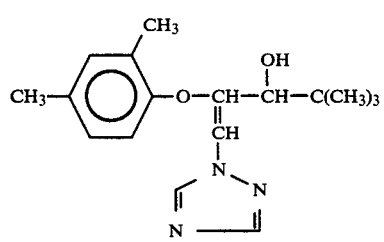 (A)

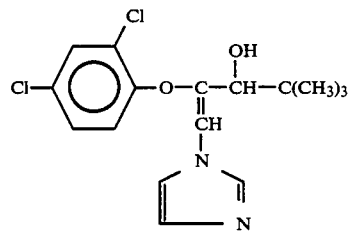 (B)

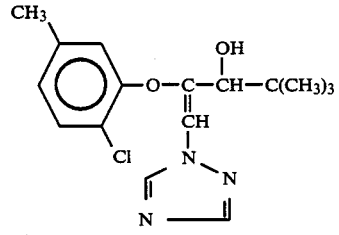 (C)

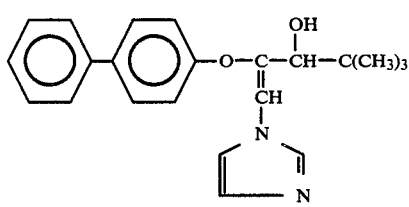 (D)

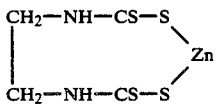 (E)

Example A

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 3 and 5.

Example B

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 5, 3, 4 and 7.

Example C

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 3, 4 and 7.

Example D

Pellicularia test (rice)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 5, 3, 4 and 7.

Example E

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 3, 5 and 4.

Example F

Botrytis test (beans)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples: 4 and 7.

It will be understood that the specification and examples are illustrative but not limitative of the present invention and that other embodiments within the spirit and scope of the invention will suggest themselves to those skilled in the art.

We claim:

1. A substituted azolyl-tetrahydrofuran-2-ylidene-methane derivative of the formula

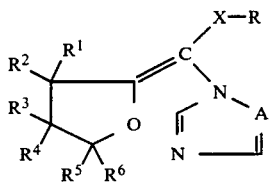

in which

A represents a nitrogen atom or the CH group;

X represents oxygen, sulphur or the SO or SO$_2$ group;

R represents phenyl which is optionally mono-, di- or tri-substituted by identical or different substituents selected from the group consisting of halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, alkoxycarbonyl with 1 to 4 carbon atoms in the alkoxy part, alkoximinoalkyl with 1 to 4 carbon atoms in the alkoxy part and 1 or 2 carbon atoms in the alkyl part, nitro, cyano and phenyl and phenoxy which are optionally substituted by halogen and/or alkyl with 1 or 2 carbon atoms;

$R^1$ to $R^6$, which can be identical or different, represent hydrogen, straight-chain or branched alkyl with 1 to 4 carbon atoms or halogenoalkyl with 1 or 2 carbon atoms and 1 to 5 identical or different halogen atoms, up to a maximum of 3 substituents representing halogenoalkyl, with the proviso that $R^1$ and $R^2$ do not at the same time represent methyl if X represents oxygen; or $R^3$ to $R^6$, which can be identical or different, also represent halogen, up to a maximum of 3 substituents having this meaning; or $R^1$ and $R^2$, together with the carbon atom to which they are bonded, represent cycloalkyl which has 4 to 7 carbon atoms and is optionally substituted by alkyl with 1 or 2 carbon atoms; or $R^2$ and $R^3$, together with the carbon atom to which they are bonded, represent cycloalkyl which has 4 to 7 carbon atoms and is optionally substituted by alkyl with 1 or 2 carbon atoms, or an addition product thereof with an acid or metal salt.

2. A substituted azolyltetrahydrofuran 2-ylidene-methane derivative or addition product according to claim 1, in which R represents phenyl which is optionally mono-, di- or tri-substituted by identical or different substituents selected from the group consisting of halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different fluorine or chlorine atoms, alkoxycarbonyl with 1 to 4 carbon atoms in the alkyl part, alkoximinoalkyl with 1 to 4 carbon atoms in the alkoxy part and 1 or 2 carbon atoms in the alkyl part, nitro, cyano and phenyl and phenoxy which are optionally substituted by halogen and/or alkyl with 1 or 2 carbon atoms;

$R^1$ to $R^6$, which can be identical or different, represent hydrogen, straight-chain or branched alkyl with 1 to 4 carbon atoms or halogenoalkyl with 1 or 2 carbon atoms and 1 to 5 identical or different fluorine or chlorine atoms, up to a maximum of 3 substituents representing halogenoalkyl, with the proviso that $R^1$ and $R^2$ do not at the same time represent methyl if X represents oxygen; or $R^3$ to $R^6$, which can be identical or different, also represent halogen, up to a maximum of 3 substituents having this meaning; or $R^1$ and $R^2$, together with the carbon atom to which they are bonded, represent cycloalkyl which has 4 to 7 carbon atoms and is optionally substituted by alkyl with 1 or 2 carbon atoms; or $R^2$ and $R^3$; together with the carbon atom to which they are bonded, represent cycloalkyl which has 4 to 7 carbon atoms and is optionally substituted by alkyl with 1 or 2 carbon atoms.

3. A substituted azolyl-tetrahydrofuran-2-ylidene-methane derivative or addition product according to claim 1, in which R represents phenyl which is optionally mono-, di- or tri-substituted by identical or different substituents selected from the group consisting of fluorine, chlorine, bromine, methyl, ethyl, tert.-butyl, methoxy, methylthio, trifluoromethyl, trifluoromethoxy, trifluoromethylthio, methoxycarbonyl, ethoxycarbonyl, methoximinomethyl, 1-methoximinoethyl, nitro, cyano and phenyl and phenoxy which are optionally substituted by chlorine and/or methyl;

$R^1$ to $R^6$ which can be identical or different, represent hydrogen, methyl, ethyl or halogenomethyl with 1 to 3 identical or different halogen atoms, such as fluorine and chlorine atoms, a maximum of three substituents representing halogenomethyl, with the proviso that $R^1$ and $R^2$ do not at the same time represent methyl if X represents oxygen; or $R^3$ to $R^6$, which can be identical or different, also represent fluorine, chlorine or bromine, up to a maximum of three substituents having this meaning; or $R^1$ and $R^2$, together with the carbon atom to which they are bonded, represent cyclopentyl or cyclohexyl; or $R^2$ and $R^3$, together with the carbon atom to which they are bonded, represent cyclopentyl or cyclohexyl.

4. A compound according to claim 1, wherein such compound is (4-chlorophenoxy)-(imidazol-1-yl)-(3-ethyl-3-methyl-tetrahydrofuran-2-ylidene)-methane of the formula

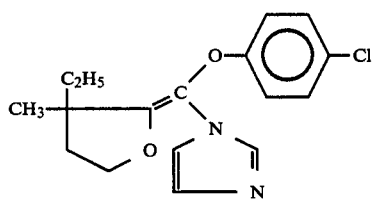

or an addition product thereof with an acid or metal salt.

5. A compound according to claim 1, wherein such compound is (4-chlorophenoxy)-(imidazol-1-yl)-(4- bromo-3,3-dimethyl-tetrahydrofuran-2-ylidene)-methane of the formula

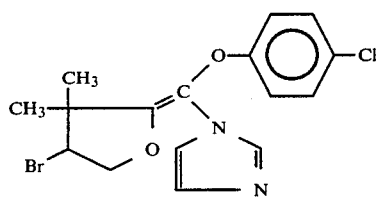

or an addition product thereof with an acid or metal salt.

6. A compound according to claim 1, wherein such compound is (2,4-dichlorophenoxy)-(imidazol-yl)-(3-ethyl-3-methyl-tetrahydrofuran-2-ylidene)-methane of the formula

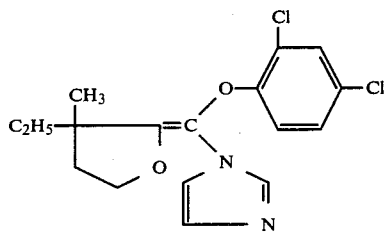

or an addition product thereof with an acid or metal salt.

7. A compound according to claim 1, wherein such compound is (2-chloro-4-fluoro-phenoxy)-(imidazol-1-yl)-(3-ethyl-3-methyl-tetrahydrofuran-2-ylidene)-methane of the formula

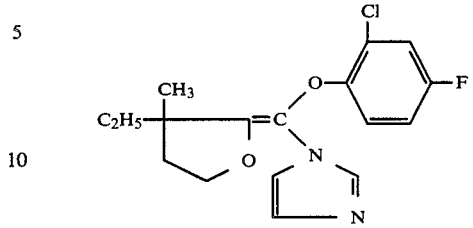

or an addition product thereof with an acid or metal salt.

8. A fungicidal composition comprising a fungicidally effective amount of a compound or addition product thereof according to claim 1 in admixture with a diluent.

9. A method of combating fungi which comprises administering to such fungi or to a habitat thereof a fungicidally effective amount of a compound or addition product thereof according to claim 1.

10. The method according to claim 9, wherein such compound is
(4-chlorophenoxy)-(imidazol-1-yl)-(3-ethyl-3-methyl-tetrahydrofuran-2-ylidene)-methane,
(4-chlorophenoxy)-(imidazol-1-yl-(4-bromo-3,3-dimethyl-tetrahydrofuran-2-ylidene)-methane,
(2,4-dichlorophenoxy)-(imidazol-yl)-(3-ethyl-3-methyl-tetrahydrofuran-2-ylidene)-methane or
(2-chloro-4-fluoro-phenoxy)-(imidazol-1-yl)-(3-ethyl-3-methyl-tetrahydrofuran-2-ylidene)-methane
or an addition product thereof with an acid or metal salt.

* * * * *